US010302594B2

(12) United States Patent
Brignac et al.

(10) Patent No.: US 10,302,594 B2
(45) Date of Patent: May 28, 2019

(54) APPARATUS AND METHOD FOR DETERMINING THE INTEGRITY OF A TUBE (71) Applicant: GENERAL ELECTRIC TECHNOLOGY GMBH, Baden (CH)

(72) Inventors: Jacques Brignac, Simsbury, CT (US); Robert Lucas, Southbury, CT (US); Gerald Hendrix, Simsbury, CT (US); Reginald Harrison, Springfield, MA (US)

(73) Assignee: GENERAL ELECTRIC TECHNOLOGY GMBH, Baden (CH)

( * ) Notice: Subject to any disclaimer, the term of this patent is extended or adjusted under 35 U.S.C. 154(b) by 186 days.

(21) Appl. No.: 15/366,736

(22) Filed: Dec. 1, 2016

(65) Prior Publication Data

US 2017/0219527 A1    Aug. 3, 2017

Related U.S. Application Data (60) Provisional application No. 62/289,482, filed on Feb. 1, 2016.

(51) Int. Cl.
G01N 27/90 (2006.01)

(52) U.S. Cl.
CPC ........ *G01N 27/902* (2013.01); *G01N 27/9013* (2013.01); *G01N 27/9046* (2013.01); *G01N 27/904* (2013.01)

(58) Field of Classification Search
CPC .... G01R 33/12; G01R 33/022; G01R 33/028; G01R 33/09; G01R 33/1253;

(Continued)

(56) References Cited

U.S. PATENT DOCUMENTS 4,625,165 A * 11/1986 Rothstein ............... G01B 7/281
324/220
4,797,613 A * 1/1989 Wentzell ............ G01N 27/9033
324/220

(Continued)

FOREIGN PATENT DOCUMENTS

| CA | 2127727 C | 12/1999 |
| EP | 0 095 845 A1 | 12/1983 |
| EP | 1 153 289 A2 | 11/2001 |

OTHER PUBLICATIONS

Extended European Search Report and Opinion issued in connection with corresponding EP Application No. 17153838.2 dated Jun. 1, 2017.

*Primary Examiner* — Vinh P Nguyen
(74) *Attorney, Agent, or Firm* — GE Global Patent Operation; Stephen G. Midgley (57) ABSTRACT

An apparatus for determining the integrity of a tube is provided. The apparatus includes: a body having an extension mechanism and configured to be inserted into the tube; and a flexible eddy current sensor including a flexible housing coupled to the body via the extension mechanism, and one or more coils disposed in the flexible housing. The flexible housing is selectively extendable via the extension mechanism between a first position and a second position. The one or more coils are farther away from the body when the flexible housing is in the second position than when the flexible housing is in the first position. The one or more coils electrically couple with an interior surface of the tube when the flexible housing is in the second position, and the flexible eddy current sensor is operative to selectively induce electrical currents within the tube via the one or more coils.

16 Claims, 6 Drawing Sheets (58) Field of Classification Search
CPC .. G01R 33/0017; G01R 33/07; G01R 33/093; G01V 3/26; G01V 3/28; G01V 3/00; G01F 1/56
See application file for complete search history.

(56) References Cited

U.S. PATENT DOCUMENTS

| | | | |
|---|---|---|---|
| 5,465,045 A | 11/1995 | DeRock | |
| 5,526,691 A | 6/1996 | Latimer et al. | |
| 5,834,937 A | 11/1998 | Burris | |
| 6,076,407 A | 6/2000 | Levesque et al. | |
| 7,528,599 B2* | 5/2009 | Zimmerman | G01N 27/9033 324/220 |
| 2006/0164091 A1* | 7/2006 | Nestleroth | G01N 27/902 324/326 |
| 2014/0002070 A1* | 1/2014 | Michaeu-Cunningham | G01N 27/902 324/240 |
| 2016/0161449 A1 | 6/2016 | Chatenet | |

\* cited by examiner

APPARATUS AND METHOD FOR DETERMINING THE INTEGRITY OF A TUBE

CROSS-REFERENCE TO RELATED APPLICATIONS

This application claims priority to U.S. Provisional Application Ser. No. 62/289,482, filed on Feb. 1, 2016 and titled "DEVICE AND METHOD FOR CRACK DETECTION IN BOILER BANK TUBE ASSEMBLY," which is incorporated herein by reference in its entirety.

BACKGROUND

Technical Field

Embodiments of the invention relate generally to boiler tubes, and more specifically, to an apparatus and method for determining the integrity of a boiler tube.

Discussion of Art

Many power generation plants utilize steam generators to power turbines which generate electrical power. Such power plants typically use boilers to generate and transport steam via boiler bank tube assemblies which include one or more tubes, referred to herein as "boiler tubes" and/or simply as "tubes," that fluidly connect an upper drum to a lower drum. The tubes of such boiler bank tube assemblies are typically fixed to the drums via a process known as expansion wherein the ends of the tubes are inserted into corresponding receiving holes on the drums, which usually have larger diameters than the tubes, and the ends of the tubes are then expanded into the drum via pneumatic expanders and rolling motors so as to form a seal between the drum and the tubes.

During boiler operations, water, and/or another medium, is heated in the tubes and/or drums such that it becomes a gas, e.g., steam, which pressurizes the tubes and drums. As such, the tubes of boiler bank tube assemblies experience thermal stresses, which may result in the emergence of new, and/or the agitation of existing, defects, e.g., thinning and/or cracking of a tube wall. Such defects in turn may degrade the integrity of the tubes, which, as used herein, refers to the likelihood that a tube will rupture and/or leak during boiler operations. For example, a tube with a high integrity is unlikely to rupture and/or leak, while a tube with a low integrity is likely to rupture and/or leak.

Generally, the likelihood that defects will develop or become agitated via thermal stress is dependent on the quality of the expansion process, i.e., the precision and consistency with respect to the shape and thickness of the ends of the tubes expanded and rolled within the drums. Many expansion processes, however, result in tubes being "over rolled," which as used herein, means the over expansion and/or over use of rolling motors that results in roll marks and/or excessively large internal diameter ("ID") ridges within the tubes. Both roll marks and/or excessively large ID ridges often form areas that experience high thermal stresses when subjected to the heat and/or pressurization of steam production, and are thus likely to result in cracking of a tube. Such cracks typically fall into two categories: 1) "circumferential cracks," which as used herein refers to cracks that generally follow the circumference of a tube, i.e., "circular cracks"; and 2) "axial cracks," which as used herein refers to cracks that generally follow the longitudinal axis of a tube, i.e., "long cracks."

As stated above, a tube with a low integrity may rupture and/or leak, which in turn may result in costly downtime of a boiler and/or cause severe physical harm and/or death to a bystander. Accordingly, many boiler tubes are regularly inspected to determine their integrity, and are subsequently repaired or replaced if found to have a significant risk of rupturing. Many methods for inspecting the integrity of such tubes, however, suffer from a variety of problems. For example, many inspection methods rely on ultrasonic shear wave technologies which are susceptible to false positives resulting from excessively large ID ridges, roll marks, and/or other geometric formations, that are inherently created in the tube by the expansion process which have not developed into cracks. Mistaking a false positive for an actual defect/crack, in turn, may result in unnecessary down time of a boiler and/or unneeded and costly maintenance.

What is needed, therefore, is an improved apparatus and method for determining the integrity of a tube.

BRIEF DESCRIPTION

In an embodiment, an apparatus for determining the integrity of a tube is provided. The apparatus includes: a body having an extension mechanism and configured to be inserted into the tube; and a flexible eddy current sensor including a flexible housing coupled to the body via the extension mechanism, and one or more coils disposed in the flexible housing. The flexible housing is selectively extendable via the extension mechanism between a first position and a second position. The one or more coils are farther away from the body when the flexible housing is in the second position than when the flexible housing is in the first position. The one or more coils electrically couple with an interior surface of the tube when the flexible housing is in the second position, and the flexible eddy current sensor is operative to selectively induce electrical currents within the tube via the one or more coils.

In another embodiment, a method for determining the integrity of a tube is provided. The method includes inserting an apparatus including a body and a flexible eddy current sensor into the tube such that the flexible eddy current sensor is inside of the tube. The body includes an extension mechanism and the flexible eddy current sensor includes a flexible housing coupled to the body via the extension mechanism, and one or more coils disposed in the flexible housing. The method further includes extending the flexible housing outwardly from the body via the extension mechanism from a first position to a second position such that the one or more coils are farther away from the body when the flexible housing is in the second position than when the flexible housing is in the first position, and such that the one or more coils electrically couple with an interior surface of the tube when the flexible housing is in the second position. The method further includes inducing electrical currents within the tube via the one or more coils.

In yet another embodiment, a flexible eddy current sensor for determining the integrity of a tube is provided. The flexible eddy current sensor includes a flexible housing that adapts to a contour of an interior surface of the tube, and a plurality of coils disposed within the flexible housing. The coils are arranged into a first group and a second group. The first group is operative to induce electrical currents within the tube so as to facilitate detection of circumferential cracks in the tube via an acquisition unit in electrical communication with the flexible eddy current sensor. The second group is operative to induce electrical currents within the tube so as to facilitate detection of axial cracks in the tube via the acquisition unit.

DRAWINGS

The present invention will be better understood from reading the following description of non-limiting embodiments, with reference to the attached drawings, wherein below.

DETAILED DESCRIPTION

Reference will be made below in detail to exemplary embodiments of the invention, examples of which are illustrated in the accompanying drawings. Wherever possible, the same reference characters used throughout the drawings refer to the same or like parts, without duplicative description.

As used herein, the terms "substantially," "generally," and "about" indicate conditions within reasonably achievable manufacturing and assembly tolerances, relative to ideal desired conditions suitable for achieving the functional purpose of a component or assembly. The term "real-time," as used herein, means a level of processing responsiveness that a user senses as sufficiently immediate or that enables the processor to keep up with an external process. As used herein, "electrically coupled," "electrically connected," "electronic communication," and "electrical communication" mean that the referenced elements are directly or indirectly connected such that an electrical current, or other communication medium, may flow from one to the other. The connection may include a direct conductive connection, i.e., without an intervening capacitive, inductive or active element, an inductive connection, a capacitive connection, and/or any other suitable electrical connection. Intervening components may be present. As also used herein, the term "fluidly connected" means that the referenced elements are connected such that a fluid (to include a liquid, gas, and/or plasma) may flow from one to the other. Accordingly, the terms "upstream" and "downstream," as used herein, describe the position of the referenced elements with respect to a flow path of a fluid and/or gas flowing between and/or near the referenced elements. As also used herein, the term "heating contact" means that the referenced objects are in proximity of one another such that heat/thermal energy can transfer between them. Further, the term "contour," as used herein with respect to a tube, refers to the shape of an interior surface of the tube. Accordingly, the terms "scan" and "scanning," as used herein, mean to search for defects within a tube.

Additionally, while the embodiments disclosed herein are described with respect to boiler tubes, it is to be understood that embodiments of the present invention may be applicable to other systems and/or processes where the integrity of a tube, other than a boiler tube, needs to be determined. Accordingly, the terms "tube," and "tubing," as used herein, means any type of tube and/or conduit, to include boiler tubes, that may develop defects, e.g., cracks and/or thinning.

Figure 1:
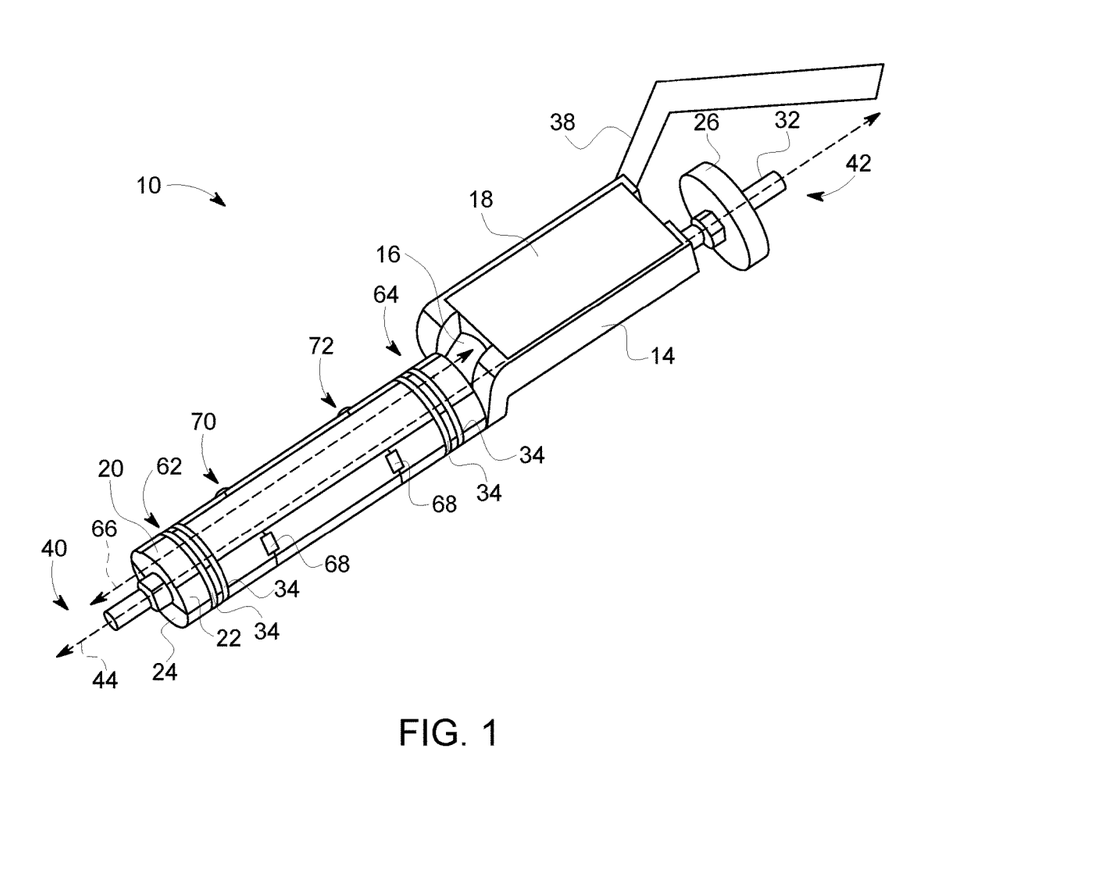
FIG. 1 is a schematic diagram of an apparatus for determining the integrity of a tube, wherein the apparatus includes a flexible eddy current sensor in accordance with an embodiment of the present invention.
Figure 2:
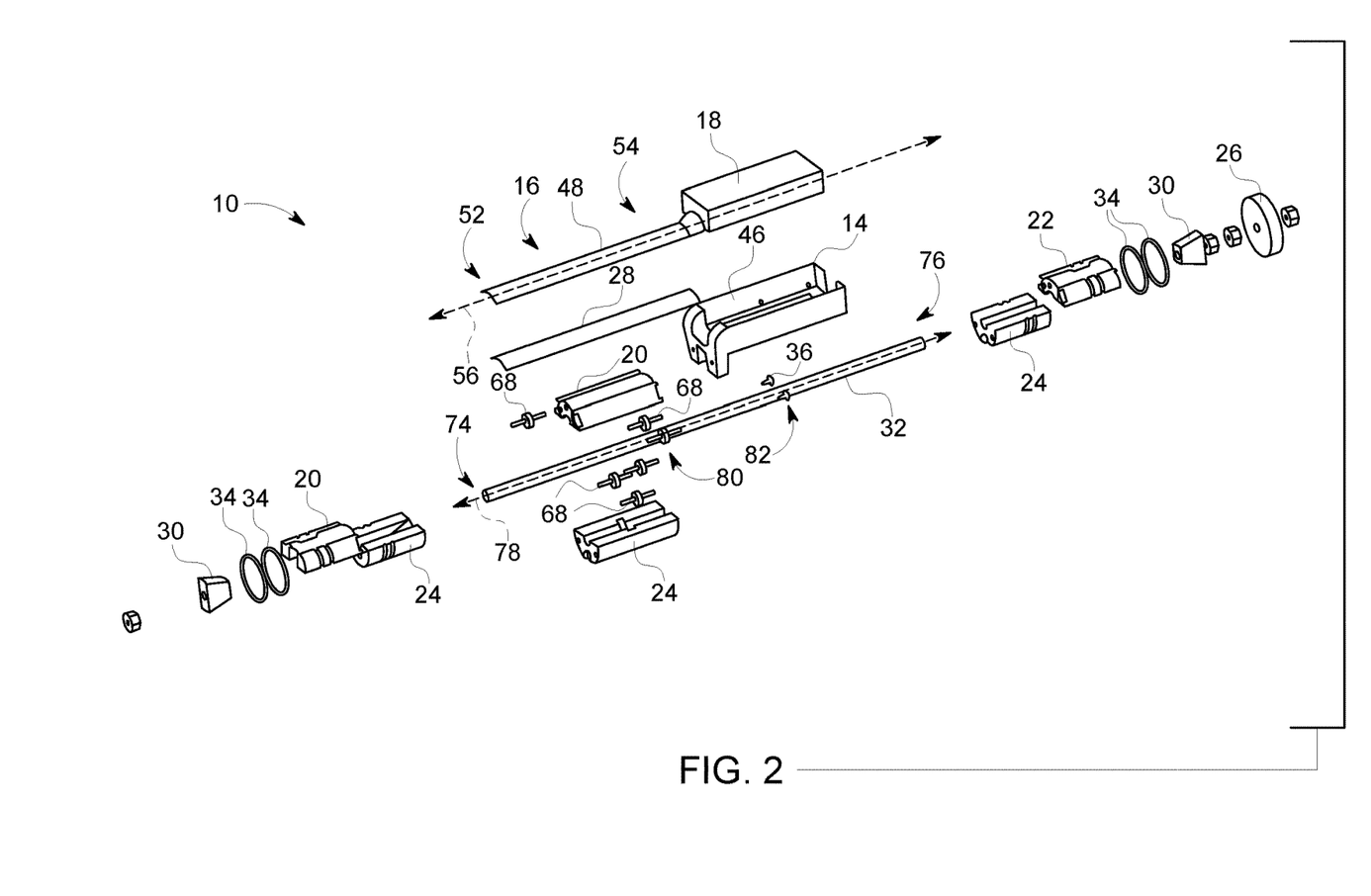
FIG. 2 is an exploded view of the apparatus of FIG. 1 in accordance with an embodiment of the present invention.

Referring now to FIGS. 1 and 2, the components of an apparatus 10 for determining the integrity of a tube 12 (FIGS. 4-7) are shown. In embodiments, the apparatus 10 includes a body 14 and a flexible eddy current sensor 16. The apparatus 10 may further include an acquisition unit 18, one or more stabilization segments 20, 22, and 24, an expansion knob 26, a foam backing 28, an extension mechanism, which in embodiments may form part of the body 14 and include one or more adjustment nuts 30 and an adjustment screw 32, one or more O-rings 34, an encoder 36, and/or a handle 38.

As shown in FIGS. 1 and 2, the body 14 is configured to be inserted into the tube 12 and may include a first end 40 and a second end 42 disposed opposite the first end 40 so as to define a longitudinal axis 44. In embodiments, the body 14 may include a cavity 46 that houses the acquisition unit 18. As will be appreciated, the body 14 may be manufactured via casting, etching, carving, additive manufacturing, i.e., 3D printing and/or any other suitable manufacturing process.

Figure 3:
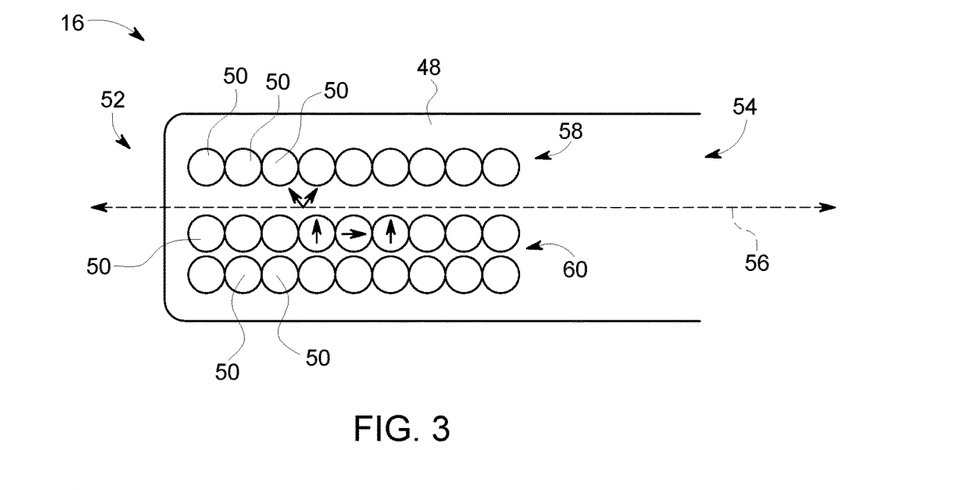
FIG. 3 is a diagram of an arrangement of coils within the flexible eddy current sensor of the apparatus of FIG. 1 in accordance with an embodiment of the present invention.

Turning now to FIGS. 2 and 3, the flexible eddy current sensor 16 may include a flexible housing 48, and one or more coils 50 disposed within the flexible housing 48. For example, in embodiments, the flexible eddy current sensor 16 includes an array of coils 50, e.g., two or more coils 50, disposed within the housing 48, i.e., the flexible eddy current sensor 16 may be a flexible array of a plurality of coils 50. The flexible housing 48 may include a first end 52 and a second end 54 disposed opposite the first end 52 so as to define a longitudinal axis 56. In embodiments, the flexible housing 48 may have a length, i.e., the spacing between the first end 52 and the second end 54, of a foot or more. It is to be understood, however, that the flexible housing 48 in other embodiments may have a longer or smaller length. As will be appreciated, the flexible housing 48 may be disposed on the body 14 and/or coupled to the body 14 via the extension mechanism such that the longitudinal axis 56 of the flexible housing 48 aligns with the longitudinal axis 44 of the body 14. In embodiments, the flexible housing 48 may be a flexible printed circuit board ("PCB") backed with a rubber compound and/or another material, such as a polyester film, that is able to support the PCB so that the PCB is not overly flimsily and/or easily ripped or torn while simultaneously allowing the PCB to remain flexible. In such embodiments, the coils 50 may be embedded into the PCB.

As is to be appreciated, the coils 50 may be formed from a conductive material, e.g., copper, such that they are capable of inducing one or more electrical currents, e.g., eddy currents, within another object, e.g., the tube 12, via magnetic induction. As shown in FIG. 3, the coils 50 may be disposed within the flexible housing 48 in a variety of arrangements which allows the apparatus 10 to detect both circumferential and axial cracks within the tube 12. For example, as further shown in FIG. 3, the coils 50 may be arranged in one or more groups 58, 60, wherein a first group 58 is configured to detect circumferential cracks and a second group 60 is configured to detect axial cracks. While the groups 58 and 60 are depicted herein as having a generally rectangular arrangement, in other embodiments, the coils 50 may be arranged in the array in a circular, triangular, and/or any other pattern suitable for generating eddy currents capable of detecting defects within the tube 12.

Returning back to FIGS. 1 and 2, the foam backing 28 may be disposed on the body 14 and against the flexible eddy current sensor 16 so as to support the flexible eddy current sensor 16. As will be discussed in greater detail below, the foam backing 28 may improve the ability of the coils 50 to generate/induce eddy currents in the tube 12.

The acquisition unit 18 may be disposed in the cavity 46 and be configured to electronically communicate with the coils 50 of the flexible eddy current sensor 16. While the embodiments depicted herein show the acquisition unit 18 disposed within the cavity 46, as will be understood, the acquisition unit 18 may be disposed in other locations of the body 14, or, in some embodiments, may be disposed apart from the body 14 and placed in electrical communication with the coils 50 via electrical cabling. As will be appreciated, the acquisition unit 18 may include electrical circuitry and/or at least one processor that controls the firing of the coils 50. As used herein, the term "firing," as it relates to the coils 50, refers to the direction and/or management of electrical current through the coils 50 so as to control the shape, magnitude, and/or direction of the magnetic fields generated by the coils 50, and thus, the properties of the currents induced in the tube 12. In embodiments, the acquisition unit 18 electronically communicates with the flexible eddy current sensor 16 so as to detect defects, e.g., axial and circumferential cracks, in the tube 12 based at least in part on the electrical currents induced in the tube 12 by the one or more coils 50.

As also shown in FIG. 1, the segments 20, 22, and 24 may each include a first end 62 and a second end 64 disposed opposite the first end 62 so as to define a longitudinal axis 66. As such, in embodiments, the segments 20, 22, and 24 may be disposed on the body 14 such that their longitudinal axes 66 align with the longitudinal axis 44 of the body 14, and such that the segments 20, 22, and 24 are selectively extendable outwardly from the body 14. The segments 20, 22, and 24 may also be spaced apart equidistantly around the longitudinal axis 44 of the body. For example, embodiments of the present invention may have three segments 20, 22, and 24 spaced apart from each other by approximately 120°. Further, in embodiments that include one or more segments 20, 22, and 24, the flexible eddy current sensor 16 may be integrated into one of the segments 20 (see FIGS. 6 and 7). For example, the flexible eddy current sensor 16 may be fully encased within a segment 20 and/or partially exposed, e.g., disposed within a groove on the surface of the segment 20.

Additionally, the segments 20, 22, and 24 may each include one or more rollers 68 arranged in one or more groups referred to herein as roller arrays 70, 72. For example, the rollers 68 may be arranged into two arrays 70 and 72 (best seen in FIG. 1) wherein each of the rollers 68 within an array are aligned in the same plane (best seen in FIG. 7). In other words, the rollers 68 of an array 70 or 72 may be located at the same position along the longitudinal axis 44 of the body 14. In embodiments, the rollers 68 may be spring loaded such that the springs act as shock absorbers. Further, as depicted in FIG. 2, the segments 20, 22, and 24 may themselves be formed from sub-segments.

Figure 4:
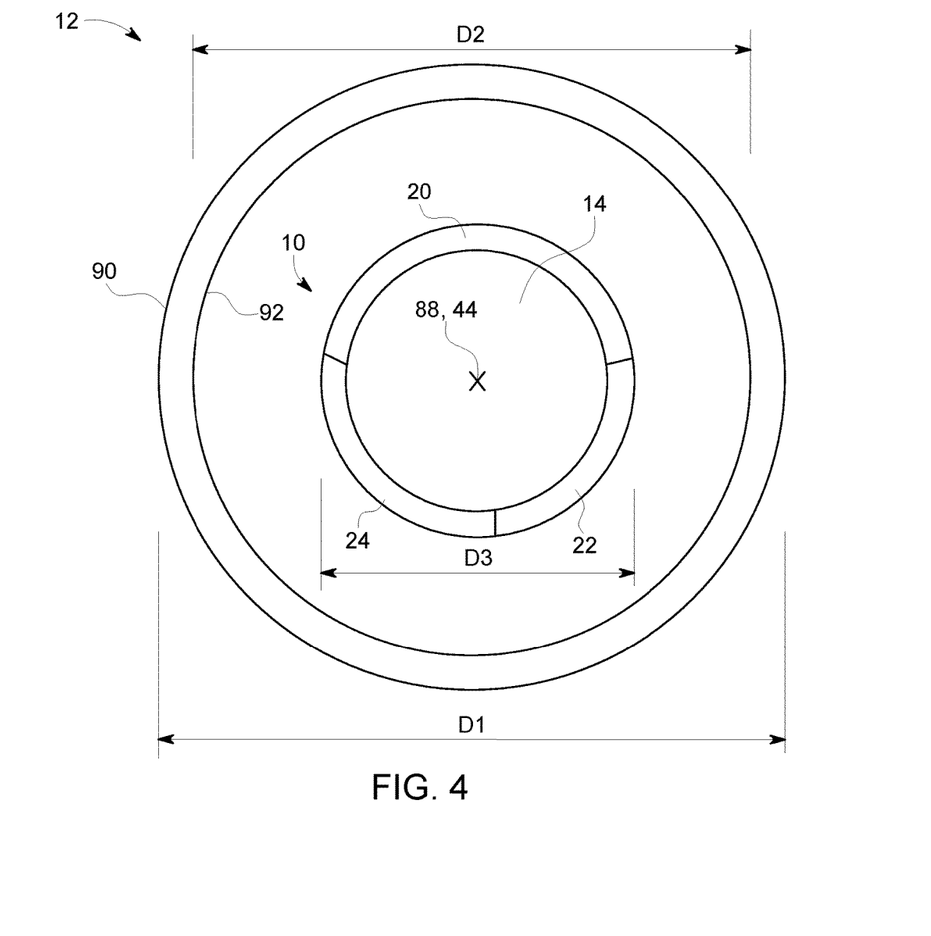
FIG. 4 is a diagram of the apparatus of FIG. 1 inserted into a tube, wherein the flexible eddy current sensor is not extended in accordance with an embodiment of the present invention.
Figure 5:
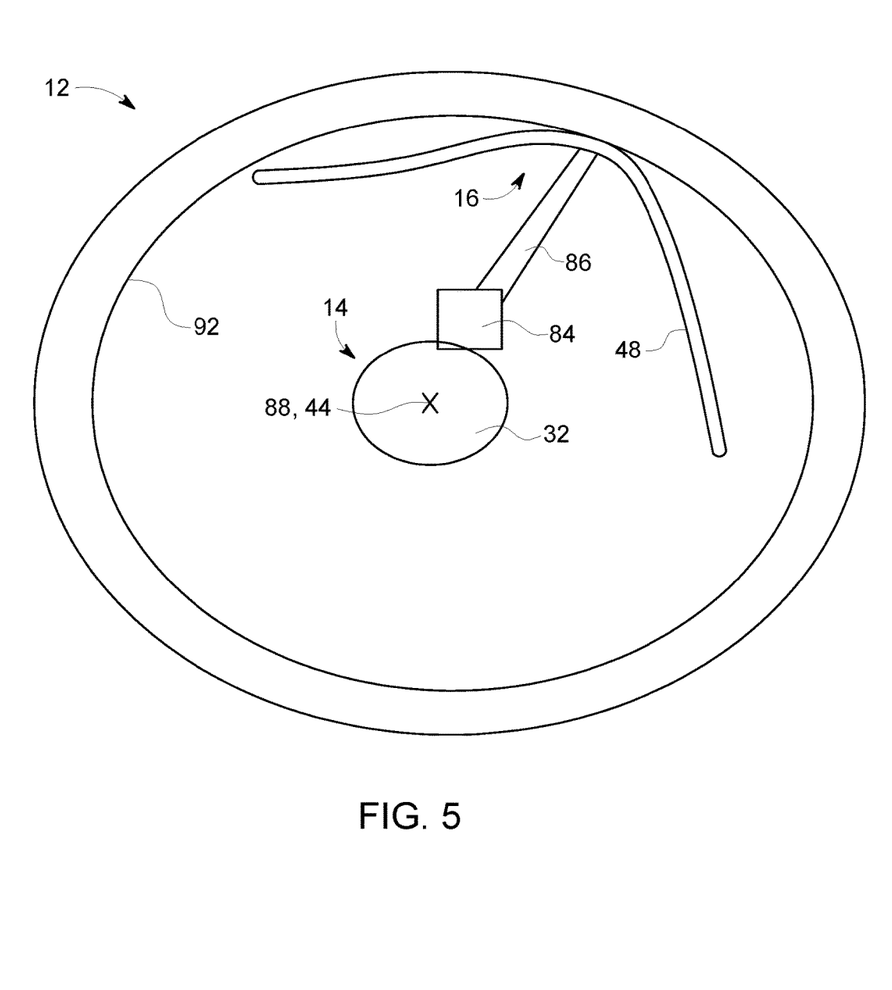
FIG. 5 is a diagram of the apparatus of FIG. 1 inserted into a tube, wherein the flexible eddy current sensor is extended in accordance with an embodiment of the present invention.
Figure 6:
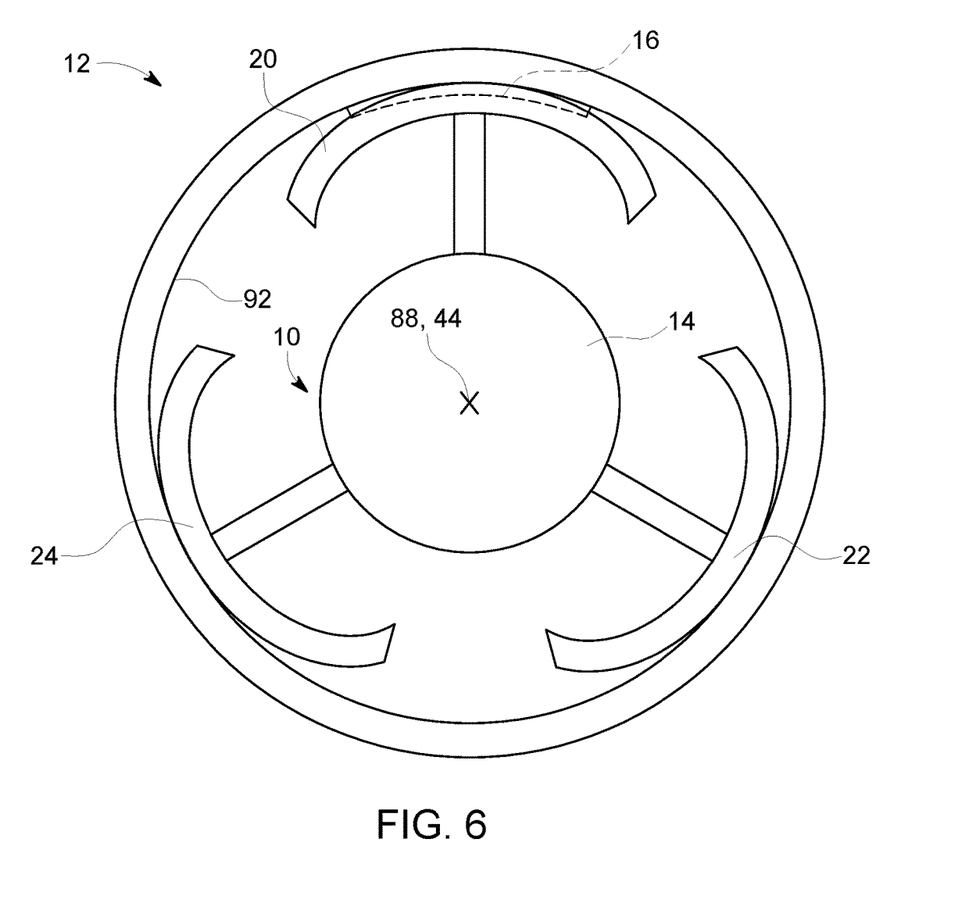
FIG. 6 is another diagram of the apparatus of FIG. 1 inserted into a tube, wherein the flexible eddy current sensor is extended in accordance with an embodiment of the present invention.
Figure 7:
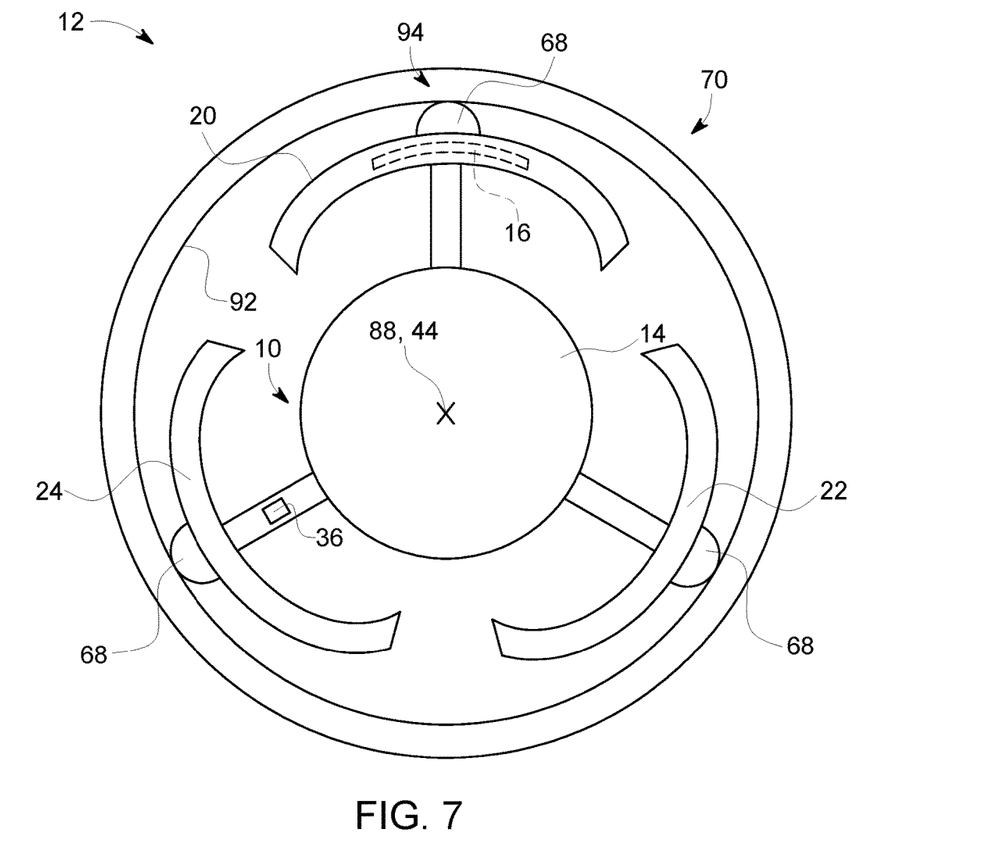
FIG. 7 is yet another diagram of the apparatus of FIG. 1 inserted into a tube, wherein the flexible eddy current sensor is extended in accordance with an embodiment of the present invention.

As stated above, in embodiments, the extension mechanism may include adjustment nuts 30 and an adjustment screw 32. The extension mechanism may also include one or more fasteners, e.g., hinges (not shown), which connect/couple the flexible housing 48 and/or segments 20, 22, and 24 to the body 14 such that the flexible housing 48 and/or segments 20, 22, and 24 can selectively extend/swing away from the body 14 while remaining connected to the body 14. In other words, in embodiments, the extension mechanism allows the flexible housing 48 to extend from a first position/retracted housing position, as shown in FIGS. 1 and 4, to a second position/extended housing position, as shown in FIGS. 5-7. In embodiments, the one or more coils 50 are farther away from the body 14 when the flexible housing 48 is in the second position than when the flexible housing 48 is in the first position.

Similarly, in embodiments, the extension mechanism allows the one or more segments 20, 22, and 24 to extend from a third position/retracted segment position, as shown in FIGS. 1 and 4, to a fourth position/extended segment position, as shown in FIGS. 6 and 7. In embodiments, a part of at least one of the one or more stabilization segments 20, 22, 24 is farther away from the body 14 in the fourth position than in the third position so as to contact the interior surface of the tube 12 when the flexible eddy current sensor 16 is in the tube 12. In embodiments, the adjustment screw 32 includes a first end 74 and a second end 76 disposed opposite the first end 74 so as to define a longitudinal axis 78, and may additionally form part of the body 14. As will be appreciated, in embodiments, the adjustment screw 32 may include one or more collapsible sections that expand and collapse so as to increase and decrease, respectively, the length of the screw 32, i.e., the length of the screw 32 may be adjustable. The adjustment screw 32 may also include a threaded pitch that interlocks with each of the adjustment nuts 30 to facilitate expansion of the flexible eddy current sensor 16/flexible housing 48 and/or the segments 20, 22, and 24. The sizing of the threaded pitch, i.e., the spacing of the thread increments, may be configured to provide for quick adjustments of the distance of extension of the flexible eddy current sensor 16/flexible housing 48, i.e., the amount that the flexible eddy current sensor 16/flexible housing 48 and/or segments 20, 22, 24 are extended away from the body 14, via a single rotation of the screw 32. In other words, small rotations of the screw 32 may result in large movements of the flexible eddy current sensor 16/flexible housing 48 and/or the segments 20, 22, and 24.

For example, in embodiments, the adjustment nuts 30 may have tapered bodies that interlock with the adjustment screw 32 such that the smaller ends of the adjustment nuts 30 face each other. In such embodiments, the adjustment screw 32 may be divided into two regions 80 and 82, wherein the threaded pitch along the second region 82 is opposite in direction to the threaded pitch along the first region 80 such that rotation of the adjustment screw 32 in a first and a second direction causes the adjustment nuts 30 to move towards and away, respectively, from each other. Accordingly, in embodiments, rotating the adjustment screw 32 in a clockwise direction may cause the adjustment nuts 30 to move towards one another such that the taper of the nuts 30 allows the nuts 30 to wedge the flexible eddy current sensor 16 and/or segments/sections 20, 22, and 24 away from the body 14 such that they swing/extend outwardly from the body 14. Similarly, rotating the adjustment screw 32 in a counterclockwise direction may move the nuts 30 away from each other such that the flexible eddy current sensor 16 and/or the segments 20, 22, and 24 retract back towards the body 14.

In other embodiments, the extension mechanism may include a base 84 (FIG. 5) having one or more expansion rods 86 (FIG. 5) which may in turn connect the flexible housing 48 and/or the segments 20, 22, and 24 to the body 14. In such embodiments, rotating the adjustment screw 32 may cause the base 84 to move along the longitudinal axis 78 of the screw 32 which in turn causes the expansion rods 86 to extend outwardly from the body 14. For example, in embodiments, the base 84 may be disposed near the second end 76 of the adjustment screw 32 such that the expansion rods 86 are retracted, i.e., not extended. In such embodiments, rotating the adjustment screw 32 clockwise may cause the base 84 to move towards the first end 74 of the adjustment screw 32 which in turn causes the expansion rods 86 to extend outwardly from the body 14. Accordingly, in such embodiments, rotating the adjustment screw 32 in a counterclockwise direction may move the base 84 back towards the second end 76 such that the expansion rods 86 retract.

As will be understood, rotation of the adjustment screw 32 may be facilitated by the expansion knob 26 which may be disposed within the apparatus 10 such that the adjustment screw 32 penetrates the knob 26. Thus, in embodiments, rotating the expansion knob 26 selectively rotates the adjustment screw 32.

The O-rings 34 may be disposed on the body 14 so as to provide a retraction force to the flexible eddy current sensor 16 and/or segments 20, 22, and 24 that restricts the flexible eddy current sensor 16 and/or segments 20, 22, and 24 from extending. Thus, as will be appreciated, the O-rings 34, in combination with the extension mechanism, e.g., adjustment nuts 30 and adjustment screw 32 or base 84 and rods 86, may stabilize the position/location of the flexible eddy current sensor 16 and/or the segments 20, 22, and 24 at a given distance of extension.

The handle 38 may be disposed on the body 14 and provides for the handling and/or transporting of the apparatus 10 by a human operator, and in embodiments, may have an ergonomic design.

Turning now to FIG. 4, the apparatus 10 inserted into the tube 12 is shown. As will be appreciated, the tube 12 may have a central axis 88 (depicted as extending out of the drawing sheet), an outer/exterior surface 90 that defines an outer/external diameter D1, and an inner/interior surface 92 that defines an inner/interior diameter D2.

As will be appreciated, in operation according to embodiments of the present invention, the apparatus 10 may be inserted into the tube 12 such that the first end 40 of the body 14 is disposed within the tube 12 with the longitudinal axis 44 of the body 14 aligning with the central axis 88 of the tube 12, i.e., the flexible eddy current sensor 16 is placed inside the tube 12. In some embodiments, the interior surface 92 may be prepared prior to inserting the body 14 into the tube, e.g., a lubricant may be applied to the interior surface 92 so as to reduce friction between the apparatus 10 and the tube 12. As will be understood, in embodiments, the apparatus 10, and components thereof, may be sized such that an external diameter D3, defined by the flexible eddy current sensor 16 and/or the segments 20, 22, and 24 when retracted, is less than the inner diameter D2 of the tube 12.

As shown in FIGS. 5 and 6, once the apparatus 10 has been inserted into the tube 12, the flexible eddy current sensor 16/flexible housing 48, and/or the segments 20, 22, and 24 may be extended outwardly from the body 14 of the apparatus 10 such that the flexible eddy current sensor 16 electrically couples with the tube 12, i.e., the one or more coils 50 form an electrical connection with the tube 12. When the one or more coils 50 form the electrical connection with the tube 12, the flexible eddy current sensor 16 can then selectively scan the tube 12 for defects by inducing electrical currents within the tube 12 via the one or more coils 50.

As stated above, the flexible eddy current sensor 16 may selectively induce eddy currents within the tube 12 via firing of the coils 50, which in turn are sensed and monitored via the acquisition unit 18 to detect the presence of defects within the tube 12. For example, in embodiments, the coils 50 may be used to both induce and sense the eddy currents within the tube 12 wherein the acquisition unit 18 receives data and/or electrical signals from the coils 50 based at least in part on the sensed eddy currents. In other embodiments, sensors apart from the coils 50 may be included within the flexible housing 48 and/or otherwise disposed on the apparatus 10 and/or tube 12 so as to detect and measure the induced eddy currents.

As illustrated in FIG. 5, the flexible nature of flexible housing 48 adjusts to a contour of the tube 12 which in turn provides for the apparatus 10 to be utilized with tubes 12 of various shapes, thicknesses, sizes and/or diameters, to include tubes having radiuses six (6) inches or less. The flexible nature of the flexible housing 48 also allows the flexible eddy current sensor 16 to be moved along the interior surface 92 while suppressing liftoff which, as used herein, refers to a situation wherein discontinuities, e.g., bumps, and/or defects in the interior surface 92 cause the flexible eddy current sensor 16 to move away from the tube 12 such that the coils 50 become decoupled from the tube 12. Accordingly, the foam backing 28, which as stated above supports the flexible eddy current sensor 16, may additionally suppress liftoff by acting as a shock absorber for the flexible eddy current sensor 16. In other words, the foam backing 28 may reduce the effects of vibrations and/or other forces imparted on the flexible eddy current sensor 16 as it moves within the tube 12.

As will also be appreciated, in embodiments, the body 14 may be configured to selectively rotate within the tube 12 such that the flexible eddy current sensor 16 sweeps the interior surface 92. As used herein, sweeping the interior surface refers to moving the flexible eddy current sensor 16 along the inner diameter D2 of the tube 12. Accordingly, the area scanned and swept by the flexible eddy current sensor 16 may be determined by the size and/or shape of the flexible eddy current sensor 16, e.g., the length and/or width of the flexible eddy current sensor 16, as well as the amount the body 14 is rotated. For example, in embodiments, the body 14 may be completely rotated such that the area scanned is the entire area of the inner surface 92 along a portion of the central axis 88 that corresponds to the length of the flexible eddy current sensor 16. Thus, as will be appreciated, in embodiments, the flexible eddy current sensor 16 is arranged to detect both circumferential cracks and axial cracks during a single rotation of the body 14.

Additionally, the depth of penetration of the flexible eddy current sensor 16 into the tube 12, i.e., the location of the flexible eddy current sensor 16 along the central axis 88 of the tube 12, may be adjustable. For example, in embodiments, the depth of penetration of the flexible eddy current sensor 16 may be adjusted by moving the body 14 from one location on the central axis 88 to another location on the central axis 88. In other embodiments, wherein the adjustable screw 32 include collapsible segments, the depth of penetration of the flexible eddy current sensor 16 into the tube 12 may be selectively adjusted by extending and/or retracting the collapsible segments.

Turning now to FIG. 7, in embodiments that include stabilization segments/sections 20, 22, and 24 having rollers 68, the segments 20, 22, and 24 may be selectively extended within the tube 12 until the rollers 68 contact the inner surface 92. Accordingly, in such embodiments, the rollers 68 may reduce the amount of friction between the apparatus 10 and the interior surface 92 as the segments 20, 22, and 24 are moved, e.g., rotated, within the tube 12, and/or may aid in centering the apparatus 10 within the tube 12. In particular, the rollers 68 in some embodiments may provide for the apparatus 10 to be centered and/or adjusted so as to compensate for variances in the contour of the inner surface 92 and/or inner diameter D2 while performing a scan. Further, as mentioned above, the rollers 68 may be spring loaded, and thus, may reduce drop-off which, as used herein, refers to the lack of and/or discontinuities in data obtained by scanning the tube 12 typically resulting from decoupling of the coils 50 from the tube 12. In other words, in embodiments, the springs in the rollers 68 act as shock absorbers which in turn increase the likelihood that the coils 50 will remain continuously coupled to the tube 12 as the body 14 is rotated during a scan.

Additionally, the acquisition unit 18 in some embodiments may be configured to determine and/or track a position/location of the flexible eddy current sensor 16 as it is moved within the tube 12. As will be understood, the acquisition unit 18 may determine and/or track the position/location of the flexible eddy current sensor 16 in real-time. Accordingly, the acquisition unit 18 may then determine the position/location of one or more detected defects, e.g., circumferential and/or axial cracks, based at least in part on the determined and/or tracked position/location of the flexible eddy current sensor 16. In such embodiments, the acquisition unit 18 may electronically communicate with the encoder 36 which measures the movement of the flexible eddy current sensor 16. As will be appreciated, in embodiments, the encoder 36 may include one or more sensors such as wheels, accelerometers, lasers, and/or other devices capable of tracking the movement and/or acceleration of the flexible eddy current sensor 16 as it moves within the tube 12. Accordingly, in such embodiments, the acquisition unit 18 and/or the encoder 36 may be "zeroed out" prior to determining and/or tracking the position/location of the flexible eddy current sensor 16. As used herein, the term "zeroed out" refers to the process of calibrating the acquisition unit 18 and/or the encoder 36 with respect to a starting position/location so that the determined and/or tracked position/location can be accurately measured.

For example, in embodiments, the apparatus 10 may be inserted into the tube 12 and rotated such that the flexible eddy current sensor 16 is aligned at a twelve O'clock position 94 of the tube 12 as shown in FIG. 7. The acquisition unit 18 may then be zeroed out such that the twelve O'clock position 94 is considered the starting position/location of the flexible eddy current sensor 16. As the body 14 is rotated, either clockwise or counter clockwise, the acquisition unit 18 is able to determine and/or track the position/location of the flexible eddy current sensor 16 at a particular point in time by adding the movement measured by the encoder 36 to the starting position/location. As will be appreciated, in embodiments, the position/location of a detected defect may be recorded/reported by the acquisition device 18 and/or encoder 36 as an angle, in radians, and/or as an absolute or relative position/location.

Further, it is also to be understood that various components of the apparatus 10, e.g., the acquisition unit 18 and/or the encoder 36, may receive power from either an external power supply and/or a power supply disposed on the apparatus, e.g., batteries and/or a generator.

Finally, it is also to be understood that the apparatus 10 may include the necessary electronics, software, memory, storage, databases, firmware, logic/state machines, microprocessors, communication links, displays or other visual or audio user interfaces, printing devices, and any other input/output interfaces to perform the functions described herein and/or to achieve the results described herein. For example, the apparatus 10 may include at least one processor and system memory/data storage structures in the form of a controller, e.g., the acquisition unit 18. The memory may include random access memory ("RAM") and read-only memory ("ROM"). The at least one processor may include one or more conventional microprocessors and one or more supplementary co-processors such as math co-processors or the like. The data storage structures discussed herein may include an appropriate combination of magnetic, optical and/or semiconductor memory, and may include, for example, RAM, ROM, flash drive, an optical disc such as a compact disc and/or a hard disk or drive.

Additionally, a software application that provides for control over one or more of the various components of the apparatus 10, e.g., the coils 50 and/or the encoder 36, may be read into a main memory of the at least one processor from a computer-readable medium. The term "computer-readable medium", as used herein, refers to any medium that provides or participates in providing instructions to the at least one processor of the apparatus 10 (or any other processor of a device described herein) for execution. Such a medium may take many forms, including but not limited to, non-volatile media and volatile media. Non-volatile media include, for example, optical, magnetic, or opto-magnetic disks, such as memory. Volatile media include dynamic random access memory ("DRAM"), which typically constitutes the main memory. Common forms of computer-readable media include, for example, a floppy disk, a flexible disk, hard disk, magnetic tape, any other magnetic medium, a CD-ROM, DVD, any other optical medium, a RAM, a PROM, an EPROM or EEPROM (electronically erasable programmable read-only memory), a FLASH-EEPROM, any other memory chip or cartridge, or any other medium from which a computer can read.

While in embodiments, the execution of sequences of instructions in the software application causes the at least one processor to perform the methods/processes described herein, hard-wired circuitry may be used in place of, or in combination with, software instructions for implementation of the methods/processes of the present invention. Therefore, embodiments of the present invention are not limited to any specific combination of hardware and/or software.

It is further to be understood that the above description is intended to be illustrative, and not restrictive. For example, the above-described embodiments (and/or aspects thereof) may be used in combination with each other. Additionally, many modifications may be made to adapt a particular situation or material to the teachings of the invention without departing from its scope.

For example, in an embodiment an apparatus for determining the integrity of a tube is provided. The apparatus includes: a body having an extension mechanism and configured to be inserted into the tube; and a flexible eddy current sensor including a flexible housing coupled to the body via the extension mechanism, and one or more coils disposed in the flexible housing. The flexible housing is selectively extendable via the extension mechanism between a first position and a second position. The one or more coils are farther away from the body when the flexible housing is in the second position than when the flexible housing is in the first position. The one or more coils electrically couple with an interior surface of the tube when the flexible housing is in the second position, and the flexible eddy current sensor is operative to selectively induce electrical currents within the tube via the one or more coils. In certain embodiments, the flexible housing is operative to adjust to a contour of the interior surface of the tube when the flexible eddy current sensor is in the tube and the flexible housing is in the second position. In certain embodiments, the body is selectively rotatable within the tube such that the flexible eddy current sensor sweeps the interior surface of the tube when the flexible housing is in the second position. In certain embodiments, the flexible eddy current sensor has two or more coils disposed in the flexible housing and arranged in an array having at least one of a rectangular shape, a circular shape, and a triangular shape. In certain embodiments, the two or more coils are arranged into a first group and a second group. The first group is operative to induce electrical currents within the tube so as to facilitate detection of circumferential cracks in the tube via an acquisition unit in electrical communication with the flexible eddy current sensor. The second group is operative to induce electrical currents within the tube so as to facilitate detection of axial cracks in the tube via the acquisition unit. In certain embodiments, the apparatus further includes an acquisition unit in electronic communication with the flexible eddy current sensor so as to detect defects in the tube based at least in part on the electrical currents induced in the tube by the one or more coils. In certain embodiments, the acquisition unit is disposed within a cavity of the body. In certain embodiments, the body is selectively rotatable within the tube such that the flexible eddy current sensor sweeps the interior surface of the tube when the flexible housing is in the second position. In such embodiments, the acquisition unit is further operative to determine a location of the flexible eddy current sensor as the flexible eddy current sensor sweeps the interior surface and to determine a location of one or more defects in the tube detected by the acquisition unit based at least in part on the determined location of the flexible eddy current sensor. In certain embodiments, the apparatus further includes one or more stabilization segments coupled to the body via the extension mechanism and selectively extendable via the extension mechanism between a third position and a fourth position. A part of at least one of the one or more stabilization segments is farther away from the body in the fourth position than in the third position so as to contact the interior surface of the tube when the flexible eddy current sensor is in the tube. In certain embodiments, the flexible eddy current sensor is integrated into one of the stabilization segments. In certain embodiments, the at least one stabilization segment includes a roller that contacts the interior surface of the tube when the one or more stabilization segments are in the fourth position. In certain embodiments, at least one of a distance of extension of the flexible housing in the second position from the body and a depth of penetration of the flexible eddy current sensor into the tube is selectively adjustable. In certain embodiments, the apparatus further includes a handle disposed on the body.

Other embodiments provide for a method for determining the integrity of a tube. The method includes inserting an apparatus including a body and a flexible eddy current sensor into the tube such that the flexible eddy current sensor is inside of the tube. The body includes an extension mechanism and the flexible eddy current sensor includes a flexible housing coupled to the body via the extension mechanism, and one or more coils disposed in the flexible housing. The method further includes extending the flexible housing outwardly from the body via the extension mechanism from a first position to a second position such that the one or more coils are farther away from the body when the flexible housing is in the second position than when the flexible housing is in the first position, and such that the one or more coils electrically couple with an interior surface of the tube when the flexible housing is in the second position. The method further includes inducing electrical currents within the tube via the one or more coils. In certain embodiments, the method further includes detecting, via an acquisition unit in electrical communication with the flexible eddy current sensor, one or more defects in the tube based at least in part on the electrical currents induced in the tube via the one or more coils. In certain embodiments, the method further includes rotating the body within the tube when the flexible housing is in the second position such that the flexible eddy current sensor sweeps the interior surface of the tube. The flexible eddy current sensor has two or more coils disposed in the flexible housing and is arranged into a first group and a second group. In such embodiments, detecting, via an acquisition unit in electrical communication with the flexible eddy current sensor, one or more defects in the tube based at least in part on the electrical currents induced in the tube via the one or more coils includes at least one of: detecting one or more circumferential cracks in the tube based at least in part on the electrical currents induced in the tube via the first group of coils; and detecting one or more axial cracks in the tube based at least in part on the electrical currents induced in the tube via the second group of coils. In certain embodiments, the method further includes determining a location of the flexible eddy current sensor via the acquisition unit; and determining a location of the one or more detected defects based at least in part on the determined location of the flexible eddy current sensor. In certain embodiments, the method further includes zeroing out the acquisition unit prior to determining the location of the flexible eddy current sensor. In certain embodiments, extending the flexible housing outwardly from the body via the extension mechanism from a first position to a second position includes extending one or more stabilization segments coupled to the body via the extension mechanism from a third position to a fourth position. A part of at least one of the one or more stabilization segments is farther away from the body in the fourth position than in the third position so as to contact the interior surface of the tube when the flexible eddy current sensor is in the tube.

Yet still other embodiments provide for a flexible eddy current sensor for determining the integrity of a tube. The flexible eddy current sensor includes a flexible housing that adapts to a contour of an interior surface of the tube, and a plurality of coils disposed within the flexible housing. The coils are arranged into a first group and a second group. The first group is operative to induce electrical currents within the tube so as to facilitate detection of circumferential cracks in the tube via an acquisition unit in electrical communication with the flexible eddy current sensor. The second group is operative to induce electrical currents within the tube so as to facilitate detection of axial cracks in the tube via the acquisition unit.

Accordingly, by utilizing a flexible eddy current sensor, some embodiments of the invention provide for an apparatus 10 that may be used to determine the integrity of a wide range of differing tubes, to include steam and mud drum generator bank tubes, which may be made from and/or of metals, carbon steel, and/or other materials in which currents may be induced via magnetic induction.

Further, by suppressing and/or eliminating liftoff and/or geometric signals resulting from over rolled tubes, some embodiments of the present invention provide for improved inspection methods that achieve more accurate results than existing systems. In particular, some embodiments of the present invention provide for an apparatus that is light in weight, easy to use in confined spaces, e.g., within a boiler, and/or provides for highly accurate and repeatable measurements of the integrity of various tubes. Additionally, the design of the apparatus of some embodiments may also provide for eased maintenance and repairs as compared to prior systems.

Further still, unlike many prior systems, the apparatus of some embodiments may determine the integrity of a tube without requiring the use of liquid penetrants and/or magnetic particles.

Moreover, by utilizing coils that detect both circumferential and axial cracks, some embodiments of the present invention provide for the ability to scan for and detect both circumferential and axial cracks within a given area of the inner surface of a tube with a single pass and/or rotation of the body and/or flexible eddy current sensor.

While the dimensions and types of materials described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, terms such as "first," "second," "third," "upper," "lower," "bottom," "top," etc. are used merely as labels, and are not intended to impose numerical or positional requirements on their objects. Further, the limitations of the following claims are not written in means-plus-function format and are not intended to be interpreted as such, unless and until such claim limitations expressly use the phrase "means for" followed by a statement of function void of further structure.

This written description uses examples to disclose several embodiments of the invention, including the best mode, and also to enable one of ordinary skill in the art to practice the embodiments of invention, including making and using any devices or systems and performing any incorporated methods. The patentable scope of the invention is defined by the claims, and may include other examples that occur to one of ordinary skill in the art. Such other examples are intended to be within the scope of the claims if they have structural elements that do not differ from the literal language of the claims, or if they include equivalent structural elements with insubstantial differences from the literal languages of the claims.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property.

Since certain changes may be made in the above-described invention, without departing from the spirit and scope of the invention herein involved, it is intended that all of the subject matter of the above description shown in the accompanying drawings shall be interpreted merely as examples illustrating the inventive concept herein and shall not be construed as limiting the invention.

What is claimed is:

1. An apparatus for determining the integrity of a tube comprising:
    a body having an extension mechanism and configured to be inserted into the tube;
    a flexible eddy current sensor including a flexible housing coupled to the body via the extension mechanism, and one or more coils disposed in the flexible housing, the flexible housing being selectively extendable via the extension mechanism between a first position and a second position, the one or more coils being farther away from the body when the flexible housing is in the second position than when the flexible housing is in the first position; and
    wherein the one or more coils electrically couple with an interior surface of the tube when the flexible housing is in the second position, and
    the flexible eddy current sensor is operative to selectively induce electrical currents within the tube via the one or more coils;
    wherein the flexible eddy current sensor has two or more coils disposed in the flexible housing and arranged in an array having at least one of a rectangular shape, a circular shape, and a triangular shape.

2. The apparatus of claim 1, wherein the flexible housing is operative to adjust to a contour of the interior surface of the tube when the flexible eddy current sensor is in the tube and the flexible housing is in the second position.

3. The apparatus of claim 1, wherein the body is selectively rotatable within the tube such that the flexible eddy current sensor sweeps the interior surface of the tube when the flexible housing is in the second position.

4. The apparatus of claim 1, wherein the two or more coils are arranged into a first group and a second group, the first group operative to induce electrical currents within the tube so as to facilitate detection of circumferential cracks in the tube via an acquisition unit in electrical communication with the flexible eddy current sensor, and the second group operative to induce electrical currents within the tube so as to facilitate detection of axial cracks in the tube via the acquisition unit.

5. The apparatus of claim 1 further comprising a handle disposed on the body.

6. An apparatus for determining the integrity of a tube comprising:
    a body having an extension mechanism and configured to be inserted into the tube;
    a flexible eddy current sensor including a flexible housing coupled to the body via the extension mechanism, and a plurality of coils disposed in the flexible housing, the flexible housing being selectively extendable via the extension mechanism between a first position and a second position, the plurality of coils being farther away from the body when the flexible housing is in the second position than when the flexible housing is in the first position; and wherein the plurality of coils electrically couple with an interior surface of the tube when the flexible housing is in the second position, the flexible eddy current sensor is operative to selectively induce electrical currents within the tube via the plurality of coils;

an acquisition unit in electronic communication with the flexible eddy current sensor to detect defects in the tube based at least in part on the electrical currents induced in the tube by the plurality of coils; wherein the body is selectively rotatable within the tube such that the flexible eddy current sensor sweeps the interior surface of the tube when the flexible housing is in the second position, and the acquisition unit is further operative to determine a location of the flexible eddy current sensor as the flexible eddy current sensor sweeps the interior surface and to determine a location of one or more defects in the tube detected by the acquisition unit based at least in part on the determined location of the flexible eddy current sensor.

7. The apparatus of claim 6, wherein the acquisition unit is disposed within a cavity of the body.

8. The apparatus of claim 6, wherein at least one of a distance of extension of the flexible housing in the second position from the body and a depth of penetration of the flexible eddy current sensor into the tube is selectively adjustable.

9. The flexible eddy current sensor of claim 6 wherein the plurality of coils is arranged into a first group and a second group, the first group operative to induce electrical currents within the tube so as to facilitate detection of circumferential cracks in the tube via an acquisition unit in electrical communication with the flexible eddy current sensor, and the second group operative to induce electrical currents within the tube to facilitate detection of axial cracks in the tube via the acquisition unit.

10. An apparatus for determining the integrity of a tube comprising:

a body having an extension mechanism and configured to be inserted into the tube;

a flexible eddy current sensor including a flexible housing coupled to the body via the extension mechanism, and one or more coils disposed in the flexible housing, the flexible housing being selectively extendable via the extension mechanism between a first position and a second position, the one or more coils being farther away from the body when the flexible housing is in the second position than when the flexible housing is in the first position; and wherein the one or more coils electrically couple with an interior surface of the tube when the flexible housing is in the second position, and the flexible eddy current sensor is operative to selectively induce electrical currents within the tube via the one or more coils;

one or more stabilization segments coupled to the body via the extension mechanism and selectively extendable via the extension mechanism between a third position and a fourth position, a part of at least one of the one or more stabilization segments being farther away from the body in the fourth position than in the third position to contact the interior surface of the tube when the flexible eddy current sensor is in the tube.

11. The apparatus of claim 10, wherein the flexible eddy current sensor is integrated into one of the stabilization segments.

12. The apparatus of claim 10 wherein the at least one stabilization segment includes a roller that contacts the interior surface of the tube when the one or more stabilization segments are in the fourth position.

13. A method for determining the integrity of a lube comprising:

inserting an apparatus including a body and a flexible eddy current sensor into the tube such that the flexible eddy current sensor is inside of the tube, the body including an extension mechanism and the flexible eddy current sensor including a flexible housing coupled to the body via the extension mechanism, and one or more coils disposed in the flexible housing;

extending the flexible housing outwardly from the body via the extension mechanism from a first position to a second position such that the one or more coils are farther away from the body when the flexible housing is in the second position than when the flexible housing is in the first position, and such that the one or more coils electrically couple with an interior surface of the tube when the flexible housing is in the second position; and inducing electrical currents within the tube via the one or more coils;

detecting, via an acquisition unit in electrical communication with the flexible eddy current sensor, one or more defects in the tube based at least in part on the electrical currents induced in the tube via the one or more coils determining a location of the flexible eddy current sensor via the acquisition unit; and determining a location of the one or more detected defects based at least in part on the determined location of the flexible eddy current sensor.

14. The method of claim 13 further comprising:

rotating the body within the tube when the flexible housing is in the second position such that the flexible eddy current sensor sweeps the interior surface of the tube; and wherein the flexible eddy current sensor has two or more coils disposed in the flexible housing and arranged, into a first group and a second group, and wherein the detecting, via an acquisition unit in electrical communication with the flexible eddy current sensor, one or more defects in the tube based at least in part on the electrical currents induced in the tube via the one or more coils comprises at least one of:

detecting one or more circumferential cracks in the tube based at least in part on the electrical currents induced in the tube via the first group of coils; and detecting one or more axial cracks in the tube based at least in part on the electrical currents induced in the tube via the second group of coils.

15. The method of claim 13 further comprising:

zeroing out the acquisition unit prior to determining the location of the flexible eddy current sensor.

16. The method of claim 13, wherein extending the flexible housing outwardly from the body via the extension mechanism from a first position to a second position comprises:

extending one or more stabilization, segments coupled to the body via the extension mechanism from a third position to a fourth position, a part of at least one of the one or more stabilization segments being farther away from the body in the fourth position than in the third position so as to contact the interior surface of the tube when the flexible eddy current sensor is in the tube.

\* \* \* \* \*